US012754586B1

(12) United States Patent
Passe

(10) Patent No.: US 12,754,586 B1
(45) Date of Patent: Oct. 6, 2026

(54) CONTROLLED-ENVIRONMENT FACILITY RESIDENT WEARABLES AND SYSTEMS AND METHODS FOR USE

(71) Applicant: Securus Technologies, LLC, Carrollton, TX (US)

(72) Inventor: Scott Passe, Forney, TX (US)

(73) Assignee: Securus Technologies, LLC, Plano, TX (US)

( * ) Notice: Subject to any disclaimer, the term of this patent is extended or adjusted under 35 U.S.C. 154(b) by 0 days.

(21) Appl. No.: 18/366,173

(22) Filed: Aug. 7, 2023

Related U.S. Application Data

(63) Continuation of application No. 18/063,743, filed on Dec. 9, 2022, now Pat. No. 11,720,146, which is a (Continued)

(51) Int. Cl.

| | |
|---|---|
| ***G06F 1/16*** | (2006.01) |
| ***A61B 5/00*** | (2006.01) |
| ***A61B 5/01*** | (2006.01) |
| ***A61B 5/024*** | (2006.01) |
| ***G08B 21/04*** | (2006.01) |
| ***G10L 15/08*** | (2006.01) |
| ***H02J 7/35*** | (2006.01) |
| ***H02J 7/80*** | (2026.01) |

(52) U.S. Cl.
CPC ............ *G06F 1/163* (2013.01); *A61B 5/0022* (2013.01); *A61B 5/01* (2013.01); *A61B 5/02444* (2013.01); *G08B 21/0446* (2013.01); *G10L 15/08* (2013.01); *H02J 7/35* (2013.01); *H02J 7/80* (2026.01); *G10L 2015/088* (2013.01)

(58) Field of Classification Search
CPC ........................................................ G06F 1/163
See application file for complete search history.

(56) References Cited

U.S. PATENT DOCUMENTS 10,142,464 B1 * 11/2018 Cairns .................. H04M 3/493
2012/0304260 A1 * 11/2012 Steeves ................ H04L 63/083 726/5

(Continued)

*Primary Examiner* — Davetta W Goins
*Assistant Examiner* — Pameshanand Mahase
(74) *Attorney, Agent, or Firm* — Fogarty LLP

(57) ABSTRACT

Controlled-environment facility resident behavioral and/or health monitoring may employ controlled-environment facility resident wearables each having a band configured to be affixed around a portion of a controlled-environment facility resident, irremovable by the resident and may include sensor(s) configured to measure biometric(s) of the controlled-environment facility resident and one or more physical parameter(s) experienced by the wearable, with a transmitter transmitting the biometric(s) and/or the physical parameter(s) to a controlled-environment facility management system. The controlled-environment facility management system may predetermine one or more normal input levels of the biometric(s) and/or physical parameter(s), receive the transmitted biometric(s) and/or physical parameter(s), determine whether received biometric(s) and/or physical parameter(s) rises above, or falls below, the predetermined normal input level(s), and alert controlled-environment facility personnel and/or law enforcement when received physical parameter(s) and/or received biometric(s) rise above or fall below the predetermined normal input level(s).

18 Claims, 5 Drawing Sheets

Related U.S. Application Data continuation of application No. 17/006,485, filed on Aug. 28, 2020, now Pat. No. 11,550,360.

(56) References Cited

U.S. PATENT DOCUMENTS

| | | | | |
|---|---|---|---|---|
| 2014/0095207 | A1* | 4/2014 | Dhir | G16H 10/60<br>705/3 |
| 2014/0121540 | A1 | 5/2014 | Raskin | |
| 2014/0215774 | A1* | 8/2014 | Ramilo | A44B 11/10<br>24/68 J |
| 2015/0186609 | A1 | 7/2015 | Utter, II | |
| 2015/0279187 | A1* | 10/2015 | Kranz | G08B 21/0415<br>340/539.12 |
| 2015/0324181 | A1* | 11/2015 | Segal | H04W 52/0264<br>709/217 |
| 2017/0201623 | A1* | 7/2017 | Keiser | H04M 7/003 |
| 2018/0103859 | A1* | 4/2018 | Provenzano | A61B 5/0024 |
| 2018/0116597 | A1 | 5/2018 | Yu et al. | |
| 2018/0218465 | A1* | 8/2018 | Lenea | G06Q 50/18 |
| 2018/0322473 | A1* | 11/2018 | Castinado | G06Q 20/36 |
| 2019/0139148 | A1* | 5/2019 | Piel | H04W 12/06 |
| 2019/0298208 | A1 | 10/2019 | Weinstein et al. | |
| 2019/0320766 | A1* | 10/2019 | Sobol | A61B 5/681 |
| 2020/0320500 | A1* | 10/2020 | Post | G06F 1/163 |

* cited by examiner

CONTROLLED-ENVIRONMENT FACILITY RESIDENT WEARABLES AND SYSTEMS AND METHODS FOR USE

CROSS-REFERENCE TO RELATED APPLICATION

This application is a continuation of, and claims benefit of, pending U.S. patent application Ser. No. 18/063,743, filed Dec. 9, 2022, which is a continuation of U.S. patent application Ser. No. 17/006,485, filed Aug. 28, 2020, and issued as U.S. Pat. No. 11,550,360, the disclosures of which are hereby incorporated herein by reference in their entirety.

TECHNICAL FIELD

The present disclosure relates generally to controlled-environment facilities, more particularly to controlled-environment facility resident wearables and systems and methods for use thereof, and specifically to use of controlled-environment facility resident wearables for controlled-environment facility resident physiology, activity and aggression detection and monitoring in a controlled-environment facility.

BACKGROUND

According to the International Center for Prison Studies, the United States has the highest prison population per capita in the world. In 2009, for example, 1 out of every 135 U.S. residents was incarcerated. Generally, inmates convicted of felony offenses serve long sentences in prison (e.g., federal or state prisons), whereas those convicted of misdemeanors receive shorter sentences to be served in jail (e.g., county jail). In either case, while awaiting trial, a suspect or accused may remain incarcerated.

Correctional officers are generally tasked with overseeing inmates' daily tasks and conduct. For example, correctional officers generally supervise activities of inmates and enforce rules to keep order within jails or prisons. Correctional officers also typically search inmates for contraband and report on inmate conduct. These tasks can be difficult for a correctional officer since each correctional officer may oversee many inmates.

Over the past several years, the above-mentioned sharp increase in the U.S. inmate population has not been followed by a proportional increase in the number of prison or jail staff. To the contrary, budget pressures in local, state, and federal governments have made it difficult for correctional facilities to maintain an adequate number of wardens, officers, and other administration personnel. Hence, many correctional facilities are often unable to perform investigations with respect to their own inmates and provide day-to-day medical care.

With each correctional officer overseeing many inmates, it may be difficult for the correctional officer to adequately supervise each inmate's conduct. Hence, inmates may be able to engage in detrimental or illicit conduct without the correctional officer's detection. Hence, prison fights can escalate into difficult to control magnitudes; illicit communications may occur; and the like. Further, without a correctional officer's detection, there may not be a reliable witness or evidentiary source for correcting or prosecuting detrimental or illicit activities that occur.

Fights, physical or verbal, are commonplace in controlled-environment facilities and may escalate to more serious problems, even full-blown riots. Traditionally, such situations have been dealt with through segregation of specific segments of the population of a controlled-environment facility or through similar action. For example, in a correctional institution environment, members of rival gangs may be housed in separate cellblocks, pods, or the like.

Overcrowding in controlled-environment facilities such as prisons or jails lead to an even greater number of confrontations. Typical responses to such situations are "after-the-fact." That is, oftentimes, facility and/or law enforcement personnel only become aware of the altercation after one or more parties have been injured or even killed.

SUMMARY

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

The present invention is directed to systems and methods which provide controlled-environment facility resident behavioral and/or health monitoring employing a plurality of controlled-environment facility resident wearables and a controlled-environment facility management system. Each wearable has a band configured to be affixed around a portion of a controlled-environment facility resident, configured to be irremovable by the controlled-environment facility resident. The wearable further includes one or more biometric sensors configured to measure one or more biometrics of the controlled-environment facility resident and one or more physical parameter sensors configured to measure one or more physical parameters experienced by the wearable, with a transmitter configured to transmit the biometric(s) of the controlled-environment facility resident and/or the physical parameter(s) experienced by the wearable to the controlled-environment facility management system.

In various respects, the biometric(s) of the controlled-environment facility resident may include respiratory rate, blood pressure, heart rate, body temperature, and/or the like of the controlled-environment facility resident, and the physical parameter(s) may include the resident's location, ambient audio, acceleration, deceleration, ambient light, ambient temperature, and/or the like.

The wearable may further include a battery powering the wearable and a charger electrically coupled to the battery, charging the battery. The charger may employ ambient light within the controlled-environment facility to generate electricity to charge the battery, may employ a thermal differential between the resident's body temperature and an ambient temperature to generate electricity to charge the battery, and/or may employ movement of the controlled-environment facility resident wearable to generate electricity to charge the battery.

The controlled-environment facility resident wearable may be paired with a controlled-environment facility resident communication and/or data device and operation of the resident communication and/or data device may be based on the paired wearable being within a designated distance of the resident communication and/or data device. Also, the controlled-environment facility resident wearable transmitter may transmit the biometric(s) of the controlled-environment facility resident and/or the physical parameter(s) experienced by the wearable to a (paired) controlled-environment facility resident communication and/or media device or to a controlled-environment facility resident communal communication and/or media terminal. The resident communication and/or media device or the controlled-environment facility resident communal communication and/or media terminal may, in turn, transmit the biometric(s) of the controlled-environment facility resident and/or the physical parameter(s) experienced by the wearable to the controlled-environment facility management system.

The controlled-environment facility management system may predetermine one or more normal input levels of the biometric(s) of the of the controlled-environment facility resident and/or predetermine one or more normal input levels of the one or more physical parameters experienced by the wearable. Thereafter, the controlled-environment facility management system may receive the transmitted biometric(s) of the of the controlled-environment facility resident and/or the physical parameter(s) experienced by the wearable. Whereupon the controlled-environment facility management system may determine whether one or more received physical parameters experienced by the wearable rises above, or falls below, the predetermined normal input level for the physical parameter(s) and/or may determine whether one or more received biometrics of the controlled-environment facility resident rises above, or falls below, the predetermined normal input level for the biometric(s). The controlled-environment facility management system may alert at least one controlled-environment facility personnel and/or law enforcement personnel, when one or more received physical parameters experienced by the wearable rises above, or falls below, the predetermined normal input level for the physical parameter(s) and/or when one or more received biometrics of the controlled-environment facility resident rises above, or falls below, the predetermined normal input level for the biometric(s) of the controlled-environment facility resident.

For example, where at least one of the physical parameters include ambient audio, the normal input level of ambient audio may be based, at least in part, on a volume of the sound, a sharpness of sounds in the ambient audio, recognition (by the controlled-environment facility management system) of particular keywords being spoken, or the like. In other examples, where at least one of the physical parameters include acceleration or deceleration experienced by the controlled-environment facility resident wearable, the determination may be whether the acceleration rises above, or deceleration falls below the predetermined normal input level, which may indicate rapid movement of the controlled-environment facility resident wearable beyond the predetermined normal input level, or the like. In a further example where the physical parameter(s) include acceleration and/or deceleration experienced by the controlled-environment facility resident wearable, the determination that the acceleration rises above or deceleration falls below the predetermined normal input level may indicate a fall by the resident and/or lack of movement after the fall. The biometric(s) of the controlled-environment facility resident may indicate one or more of the controlled-environment facility resident's general health, sleep state, level of agitation, and level of mood.

In various embodiments, one or more of the techniques described herein may be performed by one or more computer systems. In other various embodiments, a tangible computer-readable storage medium may have program instructions stored thereon that, upon execution by one or more computer systems, cause the one or more computer systems to execute one or more operations disclosed herein. In yet other various embodiments, one or more systems may each include at least one processor and memory coupled to the processor(s), wherein the memory is configured to store program instructions executable by the processor(s) to cause the system(s) to execute one or more operations disclosed herein.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated that the conception and specific embodiment disclosed may be readily utilized as a basis for modifying or designing other structures for carrying out the same purposes of the present invention. It should also be realized that such equivalent constructions do not depart from the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

Figure 1:
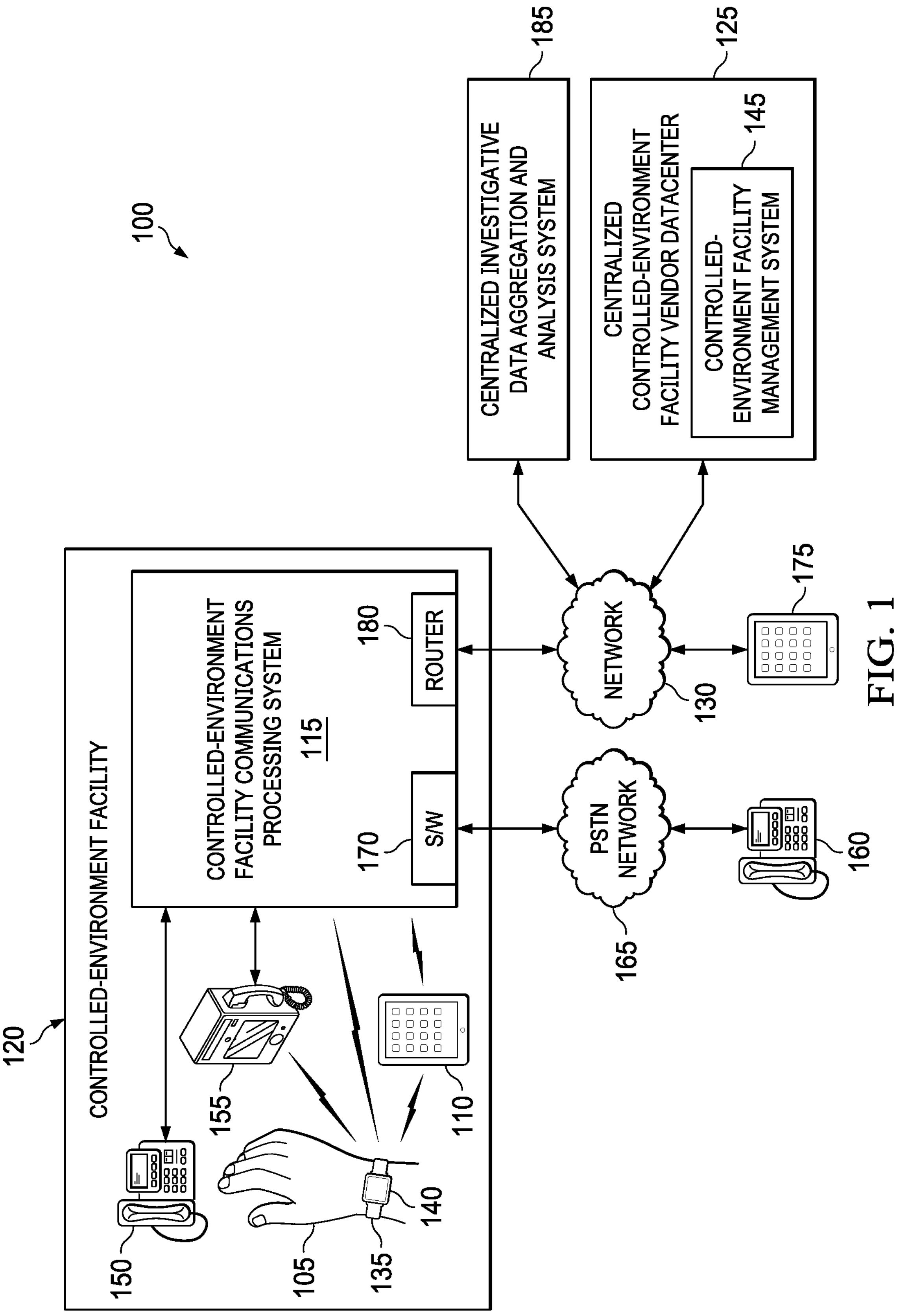
Figure 2:
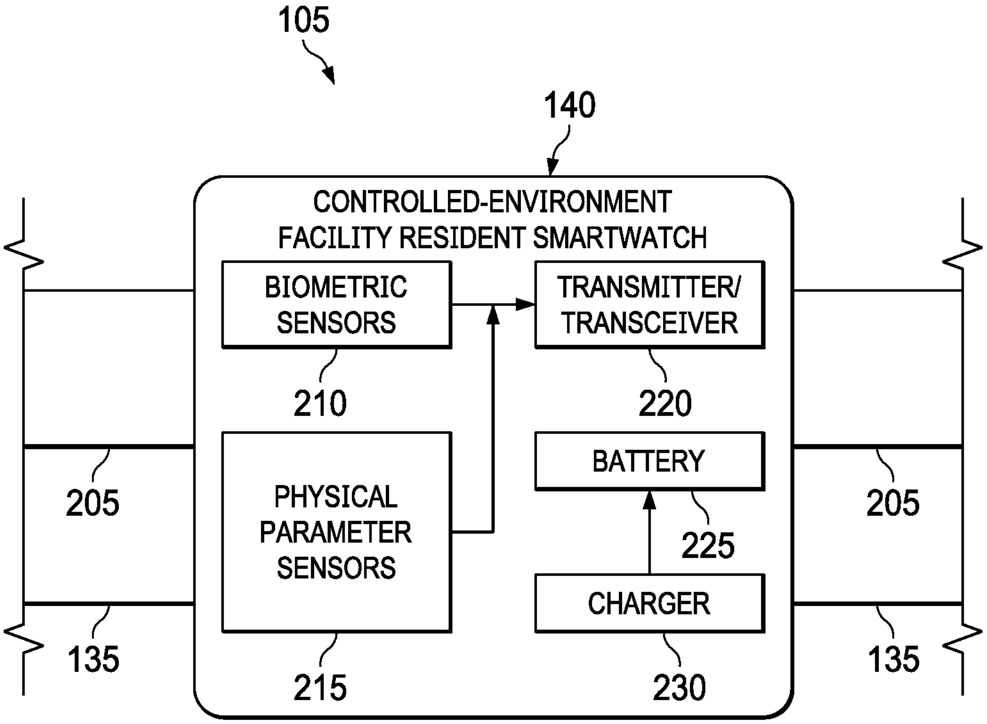
Figure 3:
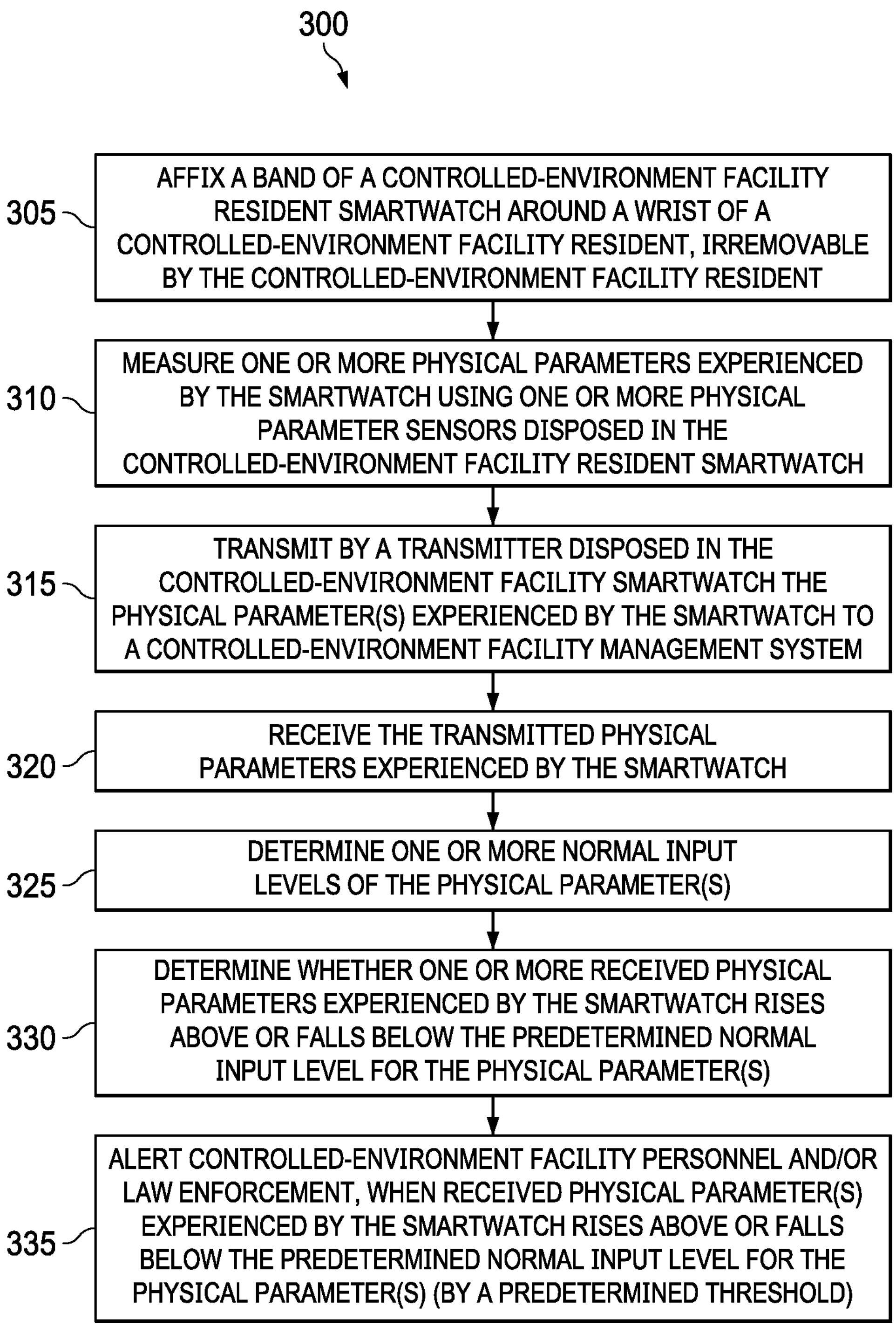
Figure 4:
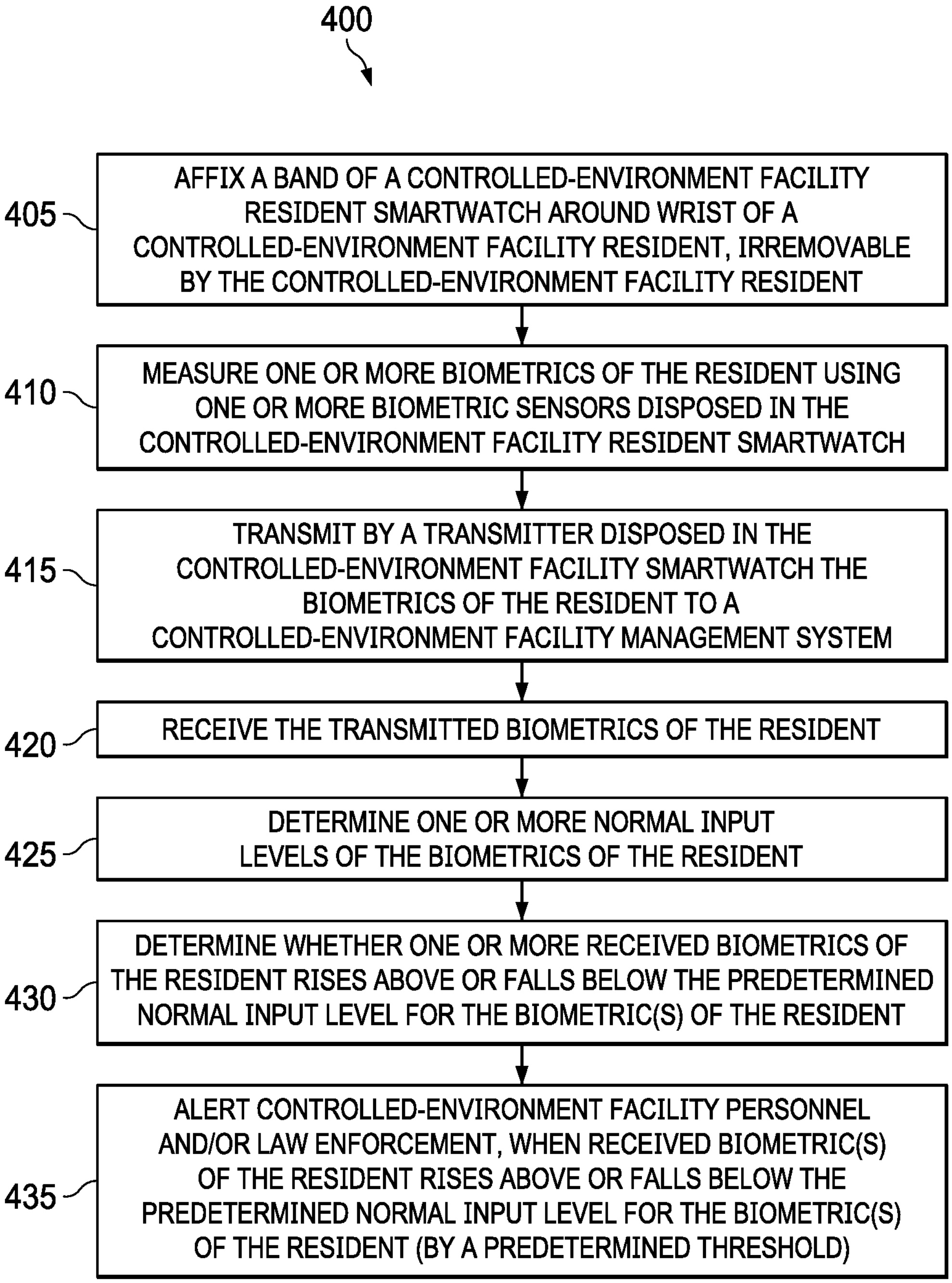
Figure 5:
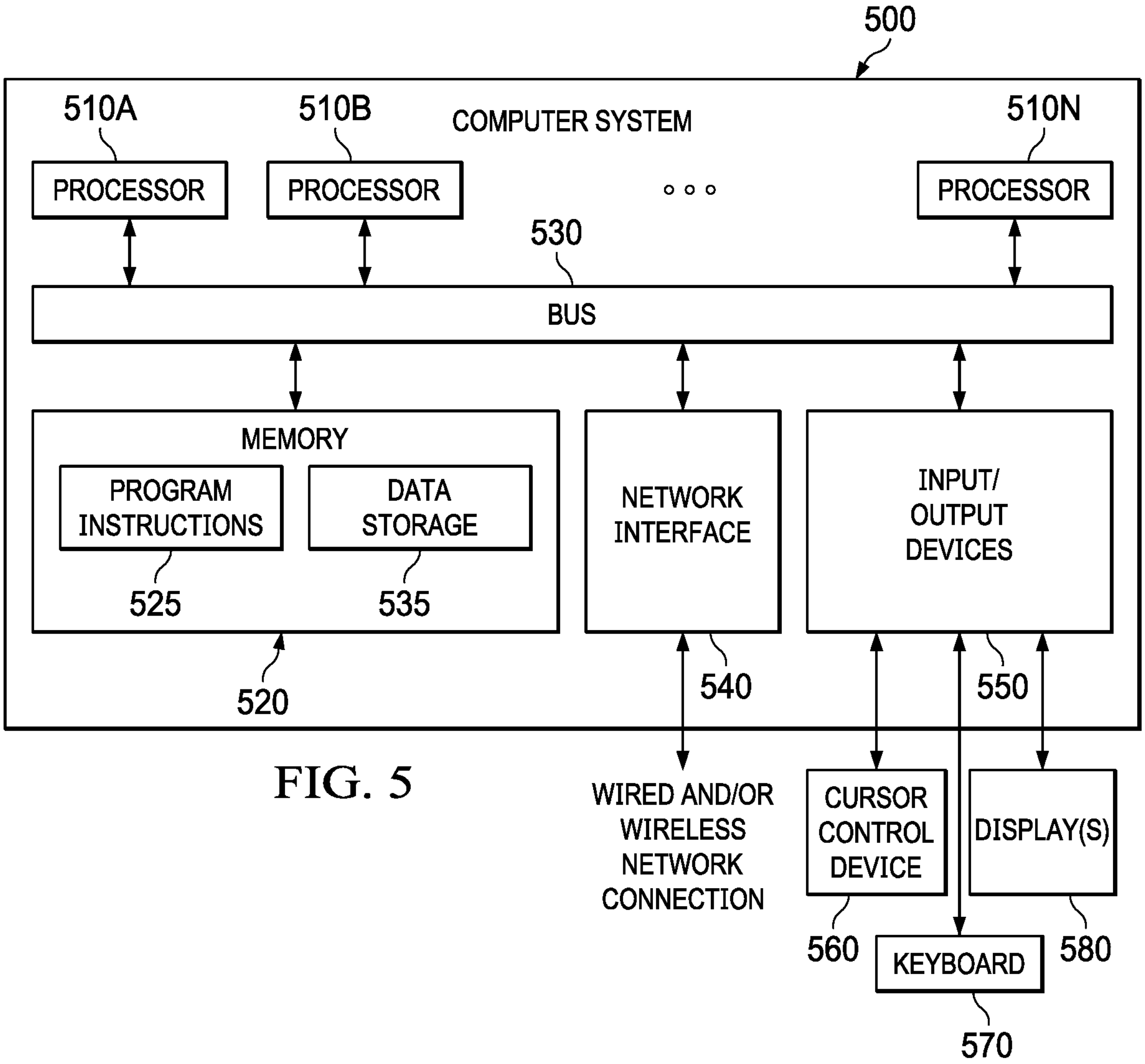

Having thus described the invention in general terms, reference will now be made to the accompanying drawings, which are not necessarily drawn to scale, and wherein:

FIG. 1 is a diagrammatic illustration of an example controlled-environment, wherein an example embodiment of the present controlled-environment facility resident wearables may be deployed in a controlled environment facility, in accordance with some embodiments;

FIG. 2 is a diagrammatic block diagram of an example embodiment of the present controlled-environment facility resident smartwatch, in accordance with some embodiments;

FIG. 3 is a flowchart of an example implementation of a process for controlled-environment facility resident monitoring using controlled-environment facility resident wearables, in accordance with some embodiments of the present systems and methods; and FIG. 4 is a flowchart of an example implementation of a process for controlled-environment facility resident behavioral monitoring, in accordance with some embodiments of the present systems and methods; and FIG. 5 is a block diagram of a computer system, device, station, or terminal configured to implement various techniques disclosed herein, according to some embodiments.

While this specification provides several embodiments and illustrative drawings, a person of ordinary skill in the art will recognize that the present specification is not limited only to the embodiments or drawings described. It should be understood that the drawings and detailed description are not intended to limit the specification to the particular form disclosed, but, on the contrary, the intention is to cover all modifications, equivalents and alternatives falling within the spirit and scope of the claims. Also, any headings used herein are for organizational purposes only and are not intended to limit the scope of the description. As used herein, the word "may" is meant to convey a permissive sense (i.e., meaning "having the potential to"), rather than a mandatory sense (i.e., meaning "must"). Similarly, the words "include," "including," and "includes" mean "including, but not limited to."

DETAILED DESCRIPTION

The invention now will be described more fully hereinafter with reference to the accompanying drawings. This invention may, however, be embodied in many different forms and should not be construed as limited to the embodiments set forth herein. Rather, these embodiments are provided so that this disclosure will be thorough and complete, and will fully convey the scope of the invention to those skilled in the art. One skilled in the art may be able to use the various embodiments of the invention.

For example, various types of controlled-environment facilities are present in today's society, and people may be voluntary or involuntary residents of such facilities, whether temporarily or permanently. Examples of controlled-environment facilities may include correctional institutions (e.g., municipal jails, county jails, state prisons, federal prisons, military stockades, juvenile facilities, detention camps, home incarceration environments, etc.), healthcare facilities (e.g., hospitals, nursing homes, mental health facilities, rehabilitation facilities, such as drug and alcohol rehabilitation facilities, etc.), restricted living quarters (e.g., hotels, resorts, camps, dormitories, barracks, etc.), and the like. For convenience of explanation, various examples discussed herein are presented in the context of correctional facilities, or the like. For instance, in some of the embodiments discussed below, a controlled-environment facility may be referred to as a correctional facility, jail or prison, and its residents may be referred to as inmates, arrestees, or detainees. It should be understood, however, that the systems and methods described herein may be similarly applicable to other types of controlled-environment facilities and their respective residents (e.g., a hospital and its patients, a school dormitory and its students, etc.).

Embodiments of the present systems and methods relates generally to controlled-environment facilities; more particularly to controlled-environment facility resident wearables and systems and methods for use thereof; and specifically, to use of controlled-environment facility resident wearables, such as smartwatches, for detection and/or monitoring controlled-environment facility resident physiology, activity and aggression. Thereby, embodiments of the present systems and methods are directed to detecting a possible event based on data indicative of one or more physical and/or physiological indicators. Hence, in accordance with embodiments of the present systems and methods, controlled-environment facility resident behavioral and/or health monitoring may employ controlled-environment facility resident wearables each having a band configured to be affixed around a portion of a controlled-environment facility resident, irremovable by the resident. The wearable may include sensor(s) configured to measure biometric(s) of the controlled-environment facility resident and one or more physical parameter(s) experienced by the wearable, with a transmitter transmitting the biometric(s) and/or the physical parameter(s) to a controlled-environment facility management system. The controlled-environment facility management system may predetermine one or more normal input levels of the biometric(s) and/or physical parameter(s), receive the transmitted biometric(s) and/or physical parameter(s), determine whether received biometric(s) and/or physical parameter(s) rises above, or falls below, the predetermined normal input level(s), and alert controlled-environment facility personnel and/or law enforcement personnel, when received physical parameter(s) and/or received biometric(s) rise above or fall below the predetermined normal input level(s).

FIG. 1 is a diagrammatic illustration of example controlled-environment 100, wherein an example embodiment of present controlled-environment facility resident wearable 105 may be deployed, in accordance with some embodiments. In accordance with embodiments of the present systems and methods, permanently, semi-permanently or temporarily affixed wearable, such as permanently, semi-permanently or temporarily affixed controlled-environment facility resident smartwatch 105, may be deployed in conjunction with or linked to (dedicatedly paired with) controlled-environment facility resident communication and/or media device 110, or the like, which may in turn be in communication with controlled-environment facility communications processing system 115. The wearable (e.g., smartwatch 105) may be "affixed" on a controlled-environment facility resident in that a band, or the like of the wearable is configured to be removed only by authorized personnel. For example, a closing system of the band may contain a locking system which may only be opened with a key or another approved method, so as to be able to take off the band without damaging or destroying the band. However, if the band is not opened with the key or another approved method, and the band is broken, deformed (e.g., stretched), or the like, an alert may be sent to controlled-environment facility personnel, such as an authorized supervisor. Thus, the controlled-environment facility wearable may be referred to herein as affixed around a wrist of a controlled-environment facility resident, or the like, "irremovable" by the controlled-environment facility resident, whether the wearable is permanently, semi-permanently or temporarily affixed on the resident. Also, herein, a controlled-environment facility resident wearable, such as by way of example controlled-environment facility resident smartwatch, may be referred to as "smartwatch 105," or the like. However, such wearables may, in accordance with embodiments of the present systems and methods, also include armband, leg or ankle band, ring, belt etc. irremovable by the controlled-environment facility resident.

In environment 100, controlled-environment facility communications processing system 115 may provide telephone services, videoconferencing, online chat, and other communication services to residents of controlled-environment facility 120. In some cases, such as illustrated, communications processing system 115 may be co-located with controlled-environment facility 120. Alternatively, or additionally, an external centralized communication processing system may be deployed in a controlled-environment facility vendor (e.g. a controlled-environment facility communications provider) datacenter 125, or the like. That is, communications processing system 115 may be centrally and/or remotely located with respect to one or more controlled-environment facilities and/or may provide communication services to multiple controlled-environment facilities, in which case, controlled-environment facility 120 is illustrated as one example. Such a controlled-environment facility vendor datacenter may be connected to such facilities via a public network (e.g. the Internet) or a private network (e.g. intranet) 130, or the like (e.g. via a secure tunneling protocol over the internet, using encapsulation). More generally, however, it should be noted that communication system 115 may assume a variety of forms, including telephony switches such as electronic switching systems, or the like, and/or and may be configured to serve a variety of facilities and/or users, whether within or outside of a controlled-environment facility.

FIG. 2 is a diagrammatic block diagram of example controlled-environment facility resident, generally permanently, semi-permanently or temporarily affixable, smartwatch 105, in accordance with some embodiments. With attention directed to both FIG. 1 and FIG. 2, it is noted that in accordance with embodiments of the present systems and methods, a controlled-environment facility resident wearable, such as by way of example controlled-environment facility resident smartwatch 105 may include band 135, or the like configured to be affixed around a wrist, or otherwise to a controlled-environment facility resident, such that the wearable is irremovable by the controlled-environment facility resident. That is, as noted above, band 135 may be configured to be removed only by authorized personnel. For example, the closing system of the band may contain a locking system which may only be opened with a key or another approved method, so as to be able to take off the band without any destruction. However, a signal on wire 205 may run through the band, and if the band, and hence the wire is cut, the band is starched so as to break or disconnect the wire, or the like an alert may be sent to controlled-environment facility personnel, such as an authorized supervisor. A signal on a wire running through other wearables such as the aforementioned armband, leg or ankle band, ring, belt etc. may also adapt these wearables to be irremovable by the controlled-environment facility resident, in accordance with embodiments of the present systems and methods.

A controlled-environment facility resident smartwatch may have watch body 140 that, in addition to providing smartwatch functions such as time telling, music (and video) player function, personal assistant functions, communications, and the like, in accordance with rules and regulations of the controlled-environment facility, such as under direction of controlled-environment facility communications processing system 115, centralized controlled-environment facility vendor datacenter 125, and/or the like, houses one or more sensors, as illustrated. However, additionally, or alternatively some or all of the sensors may be deployed in the band of the smartwatch or other wearable, and/or otherwise associated physically or communicatively with the smartwatch or other wearable. One or more of biometric sensors 210 may be configured to measure one or more biometrics of the controlled-environment facility resident and/or one or more physical parameter sensors 215 may be configured to measure one or more physical parameters experienced by the smartwatch, and therefore experienced by the controlled-environment facility resident. Transmitter (transceiver) 220 in the smartwatch body may transmit the biometric(s) of the controlled-environment facility resident and/or the physical parameter(s) experienced by the smartwatch(and the resident wearing the smartwatch) to a controlled-environment facility management system 145 such as may be housed in datacenter 125, and/or to a controlled-environment facility management system local to the resident's controlled-environment facility (120). This transmission may be carried out via a controlled-environment facility resident communication and/or media device (110) and/or controlled-environment facility communications processing system 115. Controlled-environment facility resident smartwatch 105 may be powered by battery 208, such as may be housed in watch body 140. Additionally, charger 230, also housed in watch body 140, may be electrically coupled to battery 225 for charging the battery. Charger 230 may employ ambient light within the controlled-environment facility (i.e. light in inside and/or outside spaces of the controlled-environment facility) to generate electricity to charge the battery. Additionally, or alternatively, the charger may employ a thermal differential between the resident's body temperature and an ambient temperature to generate electricity to charge the battery. In such embodiments (the) thermoelectric effect(s) may be employed for direct conversion of temperature differences to an electric voltage, via a thermocouple, to charge the battery. Furthermore, or alternatively, the charger may employ movement (e.g., motion, acceleration, deceleration, etc.) of the controlled-environment facility resident smartwatch to generate electricity to charge the battery. Vibrations from movement can also be harvested by piezoelectric materials to charge the battery, such as through use of a shunt battery charger, or the like. With respect to other wearables such as the aforementioned armband, leg or ankle band, ring, belt etc., biometric and physical parameter sensors, transmitter/transceiver, battery, charger etc. may be housed in a body of in the band (or belt) of the respective item.

The biometrics of the controlled-environment facility resident sensed and transmitted by controlled-environment facility resident smartwatch 105 may, in accordance with embodiments of the present systems and methods, include respiratory rate, blood pressure, heart rate, body temperature, blood sugar levels, and/or the like. The sensed and transmitted biometrics of the controlled-environment facility resident indicate one or more of the controlled-environment facility resident's general health, sleep state, level of agitation and/or the like. As such, a controlled-environment facility resident health monitoring system enabled by embodiments of the present controlled-environment facility resident wearable, such as example controlled-environment facility resident smartwatch 105, may predetermine one or more normal input levels of the one or more biometrics of the controlled-environment facility resident. Such a predetermination may be carried out by aforementioned controlled-environment facility management system 145, and/or the like, which may also receive the one or more biometrics of the controlled-environment facility resident transmitted by the smartwatch and determine whether one or more received biometrics of the controlled-environment facility resident rises above, or falls below, this predetermined normal input level. Controlled-environment facility management system 145, and/or the like, may alert controlled-environment facility personnel and/or other medical personnel, when one or more received biometrics of the controlled-environment facility resident rises above, or falls below, the predetermined normal input level for the corresponding one or more biometrics of the controlled-environment facility resident. This alert may only be issued when the received biometrics of the controlled-environment facility resident rises above, or falls below, the predetermined normal input level by a predetermined threshold, such as may be indicative of a medical issue, or the like. For example: increased respiratory rate could be indicative of anxiety, agitation, physical exertion, illness, physical injury or a physical altercation, or the like; decreased respiratory rate could be indicative of illness, physical injury, or the like; increased blood pressure could be indicative of agitation, illness, physical injury, a physical altercation, anxiety, or the like; decreased blood pressure could be indicative of illness, physical injury, depression (mood), or the like; increased heart rate could be indicative of agitation, physical exertion, illness, a physical altercation, physical injury, anxiety, or the like; decreased heart rate could be indicative of illness, physical injury, or the like; increased body temperature could be indicative of illness, viral or bacterial infection, or the like; decreased body temperature could be indicative of physical injury, illness, or the like; etc.

The one or more physical parameters experienced, measured and transmitted by the controlled-environment facility smartwatch may, in accordance with embodiments of the present systems and methods, include, the resident's location (within the controlled-environment facility), ambient audio, acceleration, deceleration, movement speed, other physical activity, ambient temperature, ambient light, and/or the like. As such, a controlled-environment facility resident behavioral monitoring system, enabled in accordance with embodiments of the present wearable such as example controlled-environment facility resident smartwatch 105, may predetermine one or more normal input levels of the one or more physical parameters experienced by the smartwatch and transmitted to controlled-environment facility management system 145, and/or the like. This predetermination may be carried out by aforementioned controlled-environment facility management system 145, and/or the like, which may also determine whether one or more received physical parameters experienced by the smartwatch, and hence experienced by the controlled-environment facility resident, rises above, or falls below, the predetermined normal input level for the one or more physical parameters. The controlled-environment facility management system, and/or the like, may alert controlled-environment facility personnel, law enforcement personnel, and/or the like, when one or more received physical parameters experienced by the smartwatch (and hence the controlled-environment facility resident) rises above, or falls below, the predetermined normal input level for the one or more physical parameters. This alert may only be issued when the received biometrics of the controlled-environment facility resident rises above, or falls below, the predetermined normal input level by a predetermined threshold, such as may be indicative of an event of interest to controlled-environment facility personnel, law enforcement personnel, and/or the like. For example, the resident's transmitted location may indicate the resident is in a restricted area, and/or the transmitted location could be used to perform a "bed check" to ensure the resident is in the correct room/cell at bedtime. Transmitted ambient audio may be monitored for volume levels above, or in some instances below, a normal input level of ambient audio, a sharp noise that may be indicative of a physical altercation, and/or the like. Such sharp sounds may exhibit harsh suddenness, such as compared with normal sound input levels such as may be experienced in a controlled-environment facility. For example, the ambient sound level in a controlled-environment facility cafeteria area during lunch will be much louder and full of sharper noise events than while the resident is in a sleeping area, or the like. Additionally, or alternatively, ambient audio may be monitored for word spotting, such as by controlled-environment facility management system, 145 of the like, for particular keywords being spoken in the vicinity of the smartwatch, and thus being spoken by the resident or in the vicinity (transmitted location) of the resident. For example, sounds indicative of a fight may be picked up as ambient audio, such as word spotting picking up (a) threat(s), preemptive of a fight, or the like. A determination that transmitted acceleration and/or deceleration parameters rise above or fall below the predetermined normal input level may indicate rapid movement of the controlled-environment facility resident smartwatch beyond such predetermined normal input levels, indicative of a physical confrontation, or other physical even such as a punch, fall or jump by the resident. increased speed of motion, or other physical activity may be indicative of escape, or the like. Increased ambient temperature may be indicative of a fire, or the like, while low room temperature could be indicative of a heating system failure, presence of the resident in a location they should not be (e.g. outside at night), as well as, or alternatively to measurement of ambient light, etc.

Further, in accordance with embodiments of the present systems and methods, sensed and transmitted physical parameters may be indicative of a medical issue, particularly when taken in conjunction with biometrics. For example, acceleration and/or deceleration experienced by the controlled-environment facility resident smartwatch, and hence the resident, such as may be determined to rise above or fall below the predetermined normal input level may indicate a fall by the resident, and lack of movement (i.e., sensed and transmitted motion, acceleration, deceleration, etc.) after the fall may indicate an injury or other medical condition, particularly, when viewed in light of the resident's sensed and transmitted biometrics. Likewise, one or more sensed and transmitted biometrics may be indicative of a behavioral issue such as a confrontation, fight, or the like. For example, an elevated heart rate, blood pressure, or the like, particularly accompanied by sensed and transmitted rapid acceleration and/or deceleration, may be indicative of a physical confrontation, fight, or the like. In another example, a sickness, such as a viral or bacterial infection could be indicated by an elevated temperature with lethargic (below normal), little or no movement. In a further example, the wearable may, as noted measure light, which if the resident is supposed to be outside and its daytime but the wearable is picking up on darkness, could indicate a problem such as illness, depression (mood), or the like, particularly if detected in combination with other physical parameters and/or biometrics.

Returning generally to FIG. 1, controlled-environment facility residents may use more-or-less conventional telephones 150 to access certain communication services. However, in accordance with embodiments of the present systems and methods, residents may also use a controlled-environment facility resident communication and/or media device 110, or the like, such as in conjunction with present controlled-environment facility resident smartwatch or other wearable 105, which as noted, may be dedicated to (restricted to use with) a particular controlled-environment facility resident communication and/or media device. Present controlled-environment facility resident smartwatch or other wearable 105 and controlled-environment facility resident communication and/or media device 110 may wirelessly communicate, and controlled-environment facility resident smartwatch or other wearable 105 may communicate, wirelessly, with controlled-environment facility communications processing system 115, directly, or through (paired) controlled-environment facility resident communication and/or media device 110. Personal computer wireless devices, such as a tablet computing device or smartphone (110) and/or present controlled-environment facility resident smartwatch or other wearable 105, may have been adapted and/or configured for use in a controlled-environment facility, and hence, may be used by controlled-environment facility residents for communication. Such a personal resident device may be referred to as an Intelligent Resident Device (IRD), "controlled-environment facility personal communication and/or media device," or the like, in controlled-environment facilities, in general. These may include "controlled-environment facility personal resident communication and/or media devices," and may be referred to as an Intelligent Inmate Device (IID), "inmate personal communications and/or media device," or the like, in a correctional institution environment.

Additionally, or alternatively, a resident may use a "controlled-environment facility resident communal communication and/or media terminal" 155, or the like, to place voice calls, as well as for video communication, execution of other application programs (apps), including media apps, games, job search apps, etc. Such a controlled-environment facility video communication terminal may be referred to as an Intelligent Facility Device (IFD), which may be a video phone particularly adapted and/or configured for use in a controlled-environment facility. Generally speaking, multiple controlled-environment facility resident communal communication and/or media terminals/IFDs 155 are disposed in a controlled-environment facility, and may be disposed in a visitation room, in a pod, as part of a kiosk, as an alternative to a controlled-environment facility communication kiosk, etc. Present controlled-environment facility resident smartwatch or other wearable 105, may additionally, or alternatively, be wirelessly linked with IFD 155. That is IFDs 155 may act as wireless routers in controlled-environment facility 120. Hence, present controlled-environment facility resident smartwatch or other wearable 105, may communicate wirelessly with controlled-environment facility communication processing system 115 via IFDs 155, (dedicated) IRD 110, via a controlled-environment facility wireless Local Area Network (LAN) network, and/or the like.

As will be appreciated, IRD 110, IFD 155, or other similar devices have video conferencing capabilities, or the like, to enable a party to participate in video communication sessions with other call parties, such as non-residents of the controlled-environment facility, via video communication, secure online chat, etc. In some cases, IFD 155 may assume the form of any computer, tablet computer, smart phone, etc., or any other consumer device or appliance with videoconferencing capabilities. For example, in a correctional facility environment a tablet computing device (e.g., an IRD 110) may be mounted on a wall, in a hardened case, as a controlled-environment facility resident communal communication and/or media terminal or IFD (155). IFD 155 may also take the form of a docking station adapted and/or configured to support and interface with an IRD 110 to provide communication, data, or other services.

Personal controlled-environment facility resident communication and/or media devices, IRDs 110, may be tablet computing devices, smartphones, media players, smart watches, or the like adapted and/or configured for use by residents of the controlled-environment facility (within the controlled-environment facility). Each controlled-environment facility resident smartwatch or other wearable 105 and/or IRD 110 may be particularly adapted and/or configured for use in a controlled environment. For example, in a correctional institution, jail, or the like, such an inmate smartwatch, IRD, or IID, may have a specifically adapted operating system and/or may be "stripped-down," particularly from the standpoint of what apps and/or hardware are provided or allowed on smartwatch 105 or IRD 110, and/or connectivity afforded such a smartwatch or IRD. For example, such a smartwatch or IRD may employ an operating system kernel built for use in such a smartwatch or IRD in a controlled-environment facility. As a further example, the smartwatch or IRD may be adapted to only connect to a network provided by the controlled-environment facility, and/or in only certain locations, within the controlled-environment facility, such as may be controlled by availability of wireless network access, or the like, only being available in certain areas. That is, for example, where streaming and/or downloading may be compartmentalized, leveraging the (concrete and steel) structure (i.e. construction, layout, etc.) of the controlled-environment facility, for example, limiting the availability of a wireless network signal, providing the stream through the placement of wireless access points, antenna directionality of such wireless access points, and/or the like. Further, the IRD may allow access to apps or content only upon application of security measures, by the IRD. Such security measures may include determining, by the IRD, DNS spoofing, DNS redirection, use of proxy servers for privacy and security, biometric validation, password validation, and/or the like. Also, in accordance with embodiments of the present systems and methods, the smartwatch or IRD may have a few fixed apps pre-installed on the device, and installation of further apps on the device may be forbidden (i.e. prevented by modifications to the device's operating system, or the like) and/or restricted, such as by requiring permission from a facility administrator, or the like. Apps provided on smartwatch or IRDs might include apps of particular interest to residents of the controlled-environment facility. For example, IRDs provided to inmates of correctional facilities, might include apps that may be of particular use to an inmate, in general, such as access to a legal research service, or of more specific interest, such as providing an inmate nearing release, access to employment searching apps or the like. Hence, such inmate IRDs may be used to help soon to be released inmates transition. For example, the IRD may be used to communicate with a future employer, or the like. As such, IRDs may be sponsored, or otherwise subsidized by organizations or companies, assisting with the transition of inmates into society, or the like.

In accordance with various embodiments, the controlled-environment facility resident wearable of the present systems and methods, such as smartwatch 105 may be paired, or otherwise linked with controlled-environment facility resident communication and/or data device 110, or paired with a controlled-environment facility resident communal communication and/or media terminal 155. In some such embodiments, operation of controlled-environment facility resident communication and/or data device 110 may be based on the controlled-environment facility resident smartwatch 105 being within a designated distance of the controlled-environment facility resident communication and/or data device. To wit, controlled-environment facility resident communication and/or media device 110, or a controlled-environment facility resident communal communication and/or media terminal 155, wirelessly communicatively links with wireless controlled-environment facility resident smartwatch or other wearable 105, such as by "paring" with smartwatch 105 via a short-range communication standard and respective short-range communication hardware and functionality in controlled-environment facility resident communication and/or media device 110 and smartwatch 105. Such a short-range communication standard may include UWB, Bluetooth, ZigBee, Wireless USB, LiFi (wireless communication technology which utilizes light to transmit data and position between devices), and/or the like. Upon which, smartwatch 105 may be restricted to use with controlled-environment facility resident communication and/or media device 110, or the controlled-environment facility resident communal communication and/or media terminal 155, such as by serializing the smartwatch using serial numbers of smartwatch 105 and controlled-environment facility resident communication and/or media device 110, or the controlled-environment facility resident communal communication and/or media terminal 155, during the pairing process, thereby dedicating wireless smartwatch 105 to use with controlled-environment facility resident communication and/or media device 110, or the controlled-environment facility resident communal communication and/or media terminal 155. That is, the respective smartwatch is not allowed to be "paired" or otherwise linked to another (controlled-environment facility resident communication and/or media) device or controlled-environment facility resident communal communication and/or media terminal, and vice versa, the device is not allowed to be paired with any other smartwatch 105. Controlled-environment facility communication processing system 115 and/or centralized controlled-environment facility vendor datacenter 125 may be enabled to configure wireless smartwatch 105, controlled-environment facility resident communication and/or media device 110, or the like, remotely.

Controlled-environment facility resident wearable 105 may, in accordance with some embodiments of the present systems and methods, transmit the biometric(s) of the controlled-environment facility resident and/or the physical parameter(s) experienced by the wearable to (paired) controlled-environment facility resident communication and/or media device 110 or to controlled-environment facility resident communal communication and/or media terminal 155. Resident communication and/or media device 110 or controlled-environment facility resident communal communication and/or media terminal 155 may then, in turn, transmit the biometric(s) of the controlled-environment facility resident and/or the physical parameter(s) experienced by the wearable to controlled-environment facility management system 145, such as via controlled-environment facility communications processing system 115, and/or the like.

In various embodiments, to access communication services, a resident may initiate approved telephone services by lifting the receiver on telephone 150 or IFD 155, and/or otherwise initiating a call, such as by launching a communications app on IRD 110 (or IFD 155). At which time, the resident may be prompted to provide a personal identification number (PIN), other identifying information and/or biometrics. An Interactive Voice Response (IVR) unit (not shown, but which may be integrated into communication processing system 115) may generate and play a prompt, or other messages, to the resident on device 110, 150 or 155. In accordance with various embodiments of the present systems and methods, wireless controlled-environment facility resident smartwatch or other wearable 105 may be used to provide authentication of the resident, rather than or, in addition to use of the PIN, such as by IRD 110 of IFD 155 wirelessly connecting with wireless controlled-environment facility resident smartwatch or other wearable 105 and confirming the wearable is the one permanently, semi-permanently or temporarily affixed on the calling resident. Under the control of communication processing system 115, devices 110, 150 or 155 may be capable of connecting to a non-resident's (i.e., a person not incarcerated or otherwise committed to a controlled-environment facility) telephone 160 across a Publicly Switched Telephone Network (PSTN) 165. For example, telephone 160 may be located at a non-resident's home or office, at a resident visitation center, etc. Telephony switch 170, in communication processing system 115, may be used to connect calls across PSTN 165. Additionally, or alternatively, the non-resident may communicate using device 175, which may be a mobile phone, tablet computing device, personal computer, or the like, which may be connected through an Integrated Services Digital Network (ISDN), Voice-over-IP (VoIP), or packet data network (such as, for example the Internet), a wireless communications network, or the like 130. Telephony router 180 of communication processing system 115 is used to route data packets associated with a call connection to device 175. For example, a non-resident party may have a device 175 with a built-in front-facing camera, or the like, and an integrated display (e.g., a smart phone, tablet, etc., as illustrated), a personal computer with a webcam, etc. A network connection between the parties may be established and supported by an organization or commercial service that provides computer services and software for use in telecommunications and/or VOIP, such as SKYPE®. Additionally, or alternatively, the correctional facility and/or the destination may use videoconferencing equipment compatible with ITU H.323, H.320, H.264, and/or V.80, or other suitable standards. Likewise, controlled-environment facility personnel, may send alerts to residents (inmates) or communicate with residents (inmate) via wearable 105 (and IRD 110) to provide instruction or warning, particularly in response to conditions sensed in accordance with embodiments of the present systems and methods discussed herein.

Centralized investigative data aggregation and analysis system 185 may be a platform for providing investigative tools in communication, such as via public network 130, with controlled-environment facility 120, namely controlled-environment facility communications processing system 115, and/or the like. Such investigative tools may provide collection, processing, analysis, and/or reporting of information for intelligence purposes. In some embodiments, the investigative tools may provide functions such as entity linkage analysis, communication statistics, organization analysis, communication behavior analysis, subscription usage analysis, common communication analysis, timelines, correlations, mapping, word search, language translation (whether machine translation or access to translation services), call recording (whether terminated external to the controlled-environment facility or internally thereto), call notification, call monitoring (whether real-time or recorded, and whether monitoring a particular call or a plurality of calls), call "barging," call control, visitation monitoring/background checking, crime tip conduit, account activity monitoring (whether tracing deposits and expenditures of monies or monitoring account trends and behavior, such as velocity of transactions), multiple database querying, and resource integration, and/or the like. One or more of these investigative tools may be provided through an intuitive user interface to provide ease of use, facilitate operation across a variety of user terminals, and/or to facilitate remote access to one or more features thereof. For example, in some cases, a web-based portal enabling individuals to store and transmit information, including forensic tools that analyze communications into and out of controlled-environment facilities to assist law enforcement may be provided. Such a web page portal may have menus comprising an investigator dashboard, to present and facilitate execution of various investigative operations. These investigative tools may log calls (e.g., as Call Detail Records (CDRs)), so that an investigator may research them through an archive and may be provided access to internal and/or external criminal databases and/or other sources of useful information.

Centralized investigative data aggregation and analysis system 185 may additionally, or alternatively, receive the above-described biometric(s) of the controlled-environment facility resident and/or the physical parameter(s) experienced by the smartwatch (and the resident wearing the smartwatch). As noted above, the physical parameter(s) experienced, measured and transmitted by the controlled-environment facility smartwatch may include, the resident's location (within the controlled-environment facility), ambient audio, acceleration, deceleration, movement speed, other physical activity, ambient temperature, ambient light, and/or the like. Centralized investigative data aggregation and analysis system 185 may additionally, or alternatively, alert controlled-environment facility personnel, law enforcement personnel, and/or the like, when one or more received physical parameters experienced by the smartwatch (and hence the controlled-environment facility resident) rises above, or falls below, a predetermined normal input level for the one or more physical parameters, such as by a predetermined threshold, such as may be indicative of an event of interest to controlled-environment facility personnel, law enforcement personnel, and/or the like. For example, as noted the resident's transmitted location may indicate the resident is in a restricted area and/or the transmitted location could be used to perform a "bed check" to ensure the resident is in the correct room/cell at bedtime. Transmitted ambient audio may be monitored for volume levels above, or in some instances below, a normal input level of ambient audio, a sharp noise that may be indicative of a physical altercation, and/or the like. Additionally, or alternatively, ambient audio may be monitored for word spotting by centralized investigative data aggregation and analysis system 185 for particular keywords being spoken in the vicinity of the smartwatch, and thus being spoken by the resident or in the vicinity (transmitted location) of the resident. For example, word spotting could be used to listen for confessions to criminal activity, or the like, by centralized investigative data aggregation and analysis system 185. A determination that transmitted acceleration and/or deceleration, parameters rise above or fall below the predetermined normal input level may indicate rapid movement of the controlled-environment facility resident smartwatch beyond such predetermined normal input levels, indicative of a physical confrontation, or other physical even such as a punch, fall or jump by the resident. Increased ambient temperature may be indicative of a fire, or the like, etc.

The biometrics of the controlled-environment facility resident sensed and transmitted by controlled-environment facility resident smartwatch 105 may additionally, or alternatively, be received in centralized investigative data aggregation and analysis system 185. As also noted, these biometrics may include respiratory rate, blood pressure, heart rate, body temperature, blood sugar levels, and/or the like. In accordance with embodiments of the present systems and methods, one or more sensed and transmitted biometrics may be indicative of a behavioral issue such as a confrontation, fight, or the like. For example, an elevated heart rate, blood pressure, or the like, particularly accompanied by sensed and transmitted rapid acceleration and/or deceleration, may be indicative of a physical confrontation, fight, or the like, which may be of particular interest to centralized investigative data aggregation and analysis system 185, for issuance of an alert to controlled-environment facility personnel, law enforcement personnel, and/or the like.

In addition to providing certain visitation and communication operations, communication processing system 115 may attempt to ensure that a resident's calls, video conferences, online chats, etc. are performed only with non-residents whose identities, devices, email addresses, phone numbers, etc. are listed in that resident's Pre-Approved Contact (PAC) and/or Pre-Approved Number (PAN) list. Each resident's PAC and/or PAN list(s) may be stored, for example, in (a) database(s) maintained by controlled-environment facility vendor datacenter 125, centralized investigative data aggregation and analysis system 185, and/or the like. In addition to PAC and/or PAN list(s), controlled-environment facility vendor datacenter 125, centralized investigative data aggregation and analysis system 185, and/or the like, may also store Resident Profile Data (RPD), as well as communication and/or visitation rules applicable to each resident. This controlled-environment facility vendor datacenter 125 and/or centralized investigative data aggregation and analysis system 185 database(s) may include information such as balances for resident trust and calling accounts; trial schedule; conviction data; criminal record; sentencing data, such as time served, time remaining to be served, and release date; cell and cellmate assignments; resident restrictions and warnings; commissary order history; telephone call history; call recordings; known or suspected gang or criminal affiliations; known or suspected affiliates, accomplices, or gang members; and any other information that may be relevant or useful to correctional facility staff to house and maintain residents. A controlled-environment facility resident account management system, which may be a separate system, or which may be a part or function of controlled-environment facility management system 145 of controlled-environment facility vendor datacenter 125, may maintain resident accounts to the benefit of the respective resident, such as resident commissary accounts, resident communications accounts, which may be used to pay for purchase of a controlled-environment facility resident communication and/or media device (110), (paired) controlled-environment facility resident smartwatch or other wearable 105, communications, such as phone calls, video visitation, internet chats, emails, text messages, or the like. Likewise, in accordance with some embodiments of the present systems and methods controlled-environment facility vendor datacenter 125, centralized investigative data aggregation and analysis system 185, and/or the like, particularly, a resident account management system of controlled-environment facility management system 145 may maintain information about restrictive linkages of controlled-environment facility resident communication and/or media devices (110) and respective assigned controlled-environment facility resident smartwatch or other wearable (105), including predetermined assignment of a particular controlled-environment facility resident smartwatch or other wearable 105 to a particular controlled-environment resident and/or particular controlled-environment resident communication and/or media device 110.

In some implementations, communication processing system 115 may be configured to perform communication monitoring operations, such being configured to monitor and or record communication sessions (e.g., as electronic video files). In accordance with some embodiments of the present systems and methods, controlled-environment facility 120, and/or centralized controlled-environment facility vendor datacenter 125, may issue, such as via controlled-environment facility communication processing system 115, wirelessly transmitted notifications to (via) one or more controlled-environment facility controlled-environment facility resident communication and/or media devices 110 and/or directly to one or more controlled-environment facility resident smartwatches or other wearables 105. Such direct notifications to smartwatches 105 may be sent directly to wireless smartwatches 105, such as by broadcasting the notification on (a) frequenc(y)(ies) used by the short-range protocols employed in accordance with embodiments of the present systems and methods. Controlled-environment facility resident communication and/or media device 110, and/or wireless smartwatches 105 that directly receiving the notification may interrupt play of media, by muting, pausing, terminating, etc. play of the media in a manner best suited for that media. Controlled-environment facility resident communication and/or media device 110 and/or smartwatches 105 then plays the notification.

In accordance with some embodiments of the present systems and methods, present controlled-environment facility resident smartwatch or other wearable 105 (in addition to controlled-environment facility resident communication and/or media device 110) may be able to detect short-range wireless protocol signals not associated with the detecting smartwatch (or linked controlled-environment facility resident communication and/or media device). The detecting controlled-environment facility resident smartwatch 105 may generate an alert to the controlled-environment facility (i.e. controlled-environment facility communication processing system 115, centralized controlled-environment facility datacenter 125, centralized investigative data aggregation and analysis system 185, and/or the like, to a location of the detected short-range wireless signals. In some embodiments of the present systems and methods, such alerts provided herein in response to detection of short-range wireless protocol signals, or the like, may be routed to, or via, centralized investigative data aggregation and analysis system 185, such as to alert or notify investigative personnel, other personnel associated with the controlled-environment facility (120) in which the reporting controlled-environment facility resident smartwatch is located, or the like. Additionally, or alternatively, controlled-environment facility resident smartwatch or other wearable 105, may retransmit (forward) the short-range wireless signals to the controlled-environment facility, datacenter, and/or the centralized investigative data aggregation and analysis system, for monitoring.

Likewise, contraband wireless communication device detection may use one or more controlled-environment facility resident smartwatches 105, through short-range communication protocol signal detection, and/or smartwatches 105 may each include a radio frequency detection mechanism configured to detect presence of electromagnetic energy emissions in one or more frequency bands reserved for wireless communication by wireless communication devices. In such embodiments, each controlled-environment facility resident smartwatch 105 reports detection of the presence of the electromagnetic energy emissions in one or more frequency bands reserved for wireless communication by wireless communication devices and/or short-range communication protocol signals to an investigative data aggregation and analysis system 185. The location of the reporting smartwatch(es) and/or signal strength of the emission(s) and/or short-range signals may be used by centralized investigative data aggregation and analysis system 185, or the like, to determine a location, within the controlled-environment facility, of a contraband wireless communication device emitting the electromagnetic energy emissions and/or short-range communication protocol signal. Centralized investigative data aggregation and analysis system 185, or the like, may function to determine, and/or refine, a location of a detected contraband wireless device, using location of the reporting controlled-environment facility resident smartwatch(es), signal strength(s), directionality(s) and/or the like of the detected short-range wireless protocol signals, data concerning the structure of the controlled-environment facility, triangulation, and/or the like. Such detection and determination, and/or refinement, of a location of a detected contraband wireless device is disclosed in co-pending, co-owned U.S. patent application Ser. No. 16/703,052, filed Dec. 4, 2019, which is hereby incorporated herein by reference.

Controlled-environment facility resident smartwatch or other wearable 105 may, in certain embodiments, include physical (mechanical) buttons. In accordance with various embodiments of the present systems and methods, such buttons may be used to control smartwatch functions. Additionally, or alternatively, in some embodiments, pressing a certain combination of such buttons on the wireless smartwatch may result in issuance of an emergency alert to signal an emergency to controlled-environment facility personnel, such as to a correctional facility officer.

Controlled-environment facility personnel, controlled-environment facility communication processing system 115, centralized controlled-environment facility datacenter 125, centralized investigative data aggregation and analysis system 185, and/or the like, may send alerts to residents (inmates) or communicate with residents (inmate) via wearable 105 (and IRD 110) to provide instruction or warning, particularly in response to conditions sensed in accordance with embodiments of the present systems and methods discussed herein. For example, controlled-environment facility communication processing system 115, centralized controlled-environment facility datacenter 125, centralized investigative data aggregation and analysis system 185, and/or the wearable 105, itself may automatically redirect two inmates that are not supposed to be near each other away from one another, or the like.

Computer-based environment components may include programming and/or hardware to implement embodiments of the present systems and methods. This programming may take the form of stored program instructions, programmed firmware, or the like, while hardware might take the form of an Application Specific Integrated Circuit (ASIC), or the like, to carry out such aspects of embodiments of the present systems and methods. In accordance with some embodiments of the present systems and methods, a controlled-environment facility resident smartwatch or other wearable 105, or the like, may include at least one processor and a memory coupled to the at least one processor. This memory may be configured to store program instructions executable by the at least one processor. Such program instructions may include a controlled-environment facility resident smartwatch or other wearable operating system and/or the like adapting the smartwatch for use in a controlled-environment facility.

FIG. 3 is a flowchart of an example implementation 300 of a process for controlled-environment facility resident behavioral monitoring, in accordance with some embodiments of the present systems and methods. Therein, at 305, a controlled-environment facility resident smartwatch or other wearable (105) is affixed to a controlled-environment facility resident, such as by a band (135) of a controlled-environment facility resident smartwatch (105) being affixed around a wrist of the controlled-environment facility resident, such that the smartwatch is irremovable by the controlled-environment facility resident. Sensors in, on or about the controlled-environment facility resident smartwatch or other wearable (105), generally continuously measure one or more physical parameters experienced by the smartwatch, and therefore experienced to some degree by the controlled-environment facility resident, as indicated at 310.

As indicated at 315, a transmitter or transceiver in the controlled-environment facility resident smartwatch or other wearable (105) transmits the physical parameter(s) experienced by the smartwatch to a controlled-environment facility management system (145), or the like (more or less continuously, e.g., at regular intervals). The physical parameters may include the resident's location, ambient audio, acceleration, deceleration, ambient temperature and/or the like, speed of movement, experienced by the smartwatch (and hence the controlled-environment facility resident).

The controlled-environment facility management system, or the like, (continuously) receive(s) the transmitted physical parameter(s) experienced by the smartwatch, at 320, and at 325 (or previously), determines one or more normal input levels of the physical parameter(s). The controlled-environment facility management system, or the like, then, at 330 determines whether the received physical parameters experienced by the smartwatch (and hence the controlled-environment facility resident) rises above, or falls below, the predetermined normal input level for the one or more physical parameters. For example, with respect to the physical parameter ambient audio, the normal input level of ambient audio may be based at least in part on a volume, and/or sharpness, of the sound, and may in some embodiments may also be based on location within the controlled-environment facility and/or time of day. Also, in another example where the physical parameter is ambient audio, a normal input level of the ambient audio sound may be based at least in part on recognition, by the controlled-environment facility management system of keywords being spoken. As a further example, with respect to the physical parameter being acceleration and/or deceleration experienced by the controlled-environment facility resident smartwatch, a determination at 330 that the acceleration rises above or deceleration falls below the predetermined normal input level indicates rapid movement of the controlled-environment facility resident smartwatch beyond the predetermined normal input level.

When one or more of the received physical parameters experienced by the smartwatch (and hence the controlled-environment facility resident) rises above, or falls below, the predetermined normal input level for the one or more physical parameters at 330, such as by a predetermined threshold (amount), the controlled-environment facility management system, or the like, alerts controlled-environment facility personnel, law enforcement personnel, etc., as appropriate, at 335. When the physical parameter is ambient audio and a normal input level of the ambient audio sound is based, at least in part, on recognition (i.e. word spotting), by the controlled-environment facility management system, or the like of keywords being spoken, an alert may be issued, at 335, based on one or more particular keywords being spoken, as detected at 330. For example, sounds indicative of a fight may be picked up as ambient audio, such as word spotting picking up threats, preempting fights. Likewise, word spotting could be used to listen for confessions to criminal activity, or the like.

FIG. 4 is a flowchart of example implementation 400 of a process for controlled-environment facility resident behavioral monitoring, in accordance with some embodiments of the present systems and methods. Therein, at 405, a controlled-environment facility resident smartwatch or other wearable (105) is affixed to a controlled-environment facility resident, such as by a band (135) of a controlled-environment facility resident smartwatch (105) being affixed around a wrist of the controlled-environment facility resident, such that the smartwatch is irremovable by the controlled-environment facility resident. Sensors in, on, or about the controlled-environment facility resident smartwatch or other wearable (105), generally continuously measure one or more biometrics of the controlled-environment facility resident, as indicated at 425. As indicated at 415, a transmitter or transceiver in the controlled-environment facility resident smartwatch or other wearable (105) transmits the biometrics of the controlled-environment facility resident to a controlled-environment facility management system (145), or the like (more or less continuously, e.g., at regular intervals). The biometrics may include respiratory rate, blood pressure, heart rate, body temperature, etc. of the controlled-environment facility resident.

The controlled-environment facility management system, or the like, at 420, (continuously) receive(s) the current biometrics of the resident transmitted by the smartwatch, and at 425 (or previously), determines one or more normal input levels of the resident's biometrics. The controlled-environment facility management system, or the like, then, at 430 determines whether the a received biometric of the controlled-environment facility resident rises above, or falls below, the predetermined normal input level for that biometric for the resident.

When one or more of the received biometrics of the resident rises above, or falls below, the predetermined normal input level for the one or more physical parameters at 430, such as by a predetermined threshold (amount), the controlled-environment facility management system, or the like, alerts controlled-environment facility personnel, (other) medical personnel, etc., as appropriate, at 435.

In a similar manner, controlled-environment facility resident health monitoring may make use of one or more sensed and transmitted physical parameters. For example, with respect to acceleration and/or deceleration experienced by the controlled-environment facility resident smartwatch, and thereby by the resident, a determination that the acceleration rises above or deceleration falls below the predetermined normal input level may indicate a fall by the resident and lack of movement after the fall, and thereby, a serious injury. Likewise, a combination of physical parameters and biometrics may be used in accordance with the present systems and methods. For example, as noted, sensed and transmitted physical parameters may be indicative of a medical issue when taken in conjunction with biometrics. For example, the above-detected fall may even more clearly indicate an injury or other medical condition when viewed in light of the resident's sensed and transmitted biometrics. As also noted above, one or more sensed and transmitted biometrics may be indicative of a behavioral issue such as a confrontation, fight, or the like. For example, an elevated heart rate, blood pressure, or the like, particularly accompanied by sensed and transmitted rapid acceleration and/or deceleration, may be indicative of a physical confrontation, fight, or the like. Raised body temperature could indicate a bacterial or viral infection, lowered physical activity could indicate depression (mood), lack of light could indicate suicidal concerns, or the like, etc.

In accordance with embodiments of the present systems and methods, a controlled-environment facility commissary goods ordering and distribution systems and methods that employs one or more controlled-environment facility vending machines disposed in the controlled-environment facility may also make use of the present controlled-environment facility resident wearables 105. Wearables 105 and/or controlled-environment facility resident communication and/or media devices 110 disposed in the controlled-environment facility may accept orders from residents of the controlled-environment facility for one or more commissary items and transmit the order to the controlled-environment facility vending machine(s), such as through controlled-environment facility communication processing system 115, centralized controlled-environment facility datacenter 125, or the like. The controlled-environment facility vending machine(s) may include a vending mechanism configured to selectively vend selected items and a vending controller. The vending controller may accept or retrieve the order, verify the presence of the resident at the vending machine, and cause the vending mechanism to dispense item(s) in the order, to the resident. In accordance with the present systems and methods the vending machine may "sense" the resident and vend the ordered product(s). That is to say, the vending machine may employ a nearfield communication technology or the like to detect an ordering resident's wearable 105 and vend the product(s) when it is determined the resident is immediately adjacent (and/or in front of) the vending machine, and hence in position to retrieve the product(s) from a vending slot, or the like. Alternatively, or additionally, the resident may identify him/herself to the vending machine, such as through entry of identification information, such as a number associated with the resident, a PIN, scanning a picture ID or a barcode, providing a fingerprint, an iris scan, or any other biometric identifier, and resident wearable 105 may be used by the vending controller as a second factor for authenticating the resident. Additionally, such a controlled-environment facility vending machine may include more than one radio frequency sensor or reader, such as nearfield communication devices/antennae, disposed in the vending machine, spaced apart on either side at the face of the machine, or the like, to further facilitate or confirm detection of the resident at the machine, such as in front of the machine, (i.e., "between" the readers/devices), through triangulation, or the like, of the resident (wearable 105) at the machine (in front of the machine).

Various elements of the present controlled-environment facility resident contact tools for intelligent controlled-environment facility resident communication and/or media device interfaces may be implemented as modules. Modules may be implemented in hardware. In another embodiment, modules may be expressed in software executed by hardware. In still another embodiment, modules may be implemented in firmware operated by hardware. In still other embodiments, modules may be implemented in combinations of hardware, software, and/or firmware.

Embodiments of the present systems and methods for use of controlled-environment facility resident wearables, as described herein, may be implemented at least in part as, or executed, at least in part, by one or more computer systems. One such computer system is illustrated in FIG. 5. In various embodiments, computer system 500 may be a server, a mainframe computer system, a workstation, a network computer, a desktop computer, a laptop, a tablet computing device, media player, or the like. For example, in some cases, computer 500 may implement one or more steps of example processes 300 and 400 described above with respect to FIGS. 3 and 4, and/or a computer system such as computer system 500 may be used as part of, one or more of: controlled-environment facility resident communication and/or media devices (IRDs) 110; controlled-environment facility communication processing systems 115; controlled-environment facility vendor data center 125; IFDs 155; centralized investigative data aggregation and analysis system 185; nonresident communications devices 175; and/or the like. In various embodiments two or more of these computer systems may be configured to communicate with each other in any suitable way, such as, for example, via public network 130, which may be the Internet, or the like, as discussed above, via a local area network using wired or wireless functionality, etc.

As illustrated, computer system 500 includes one or more processors 510A-N coupled to a system memory 520 via bus 530. Computer system 500 further includes a network interface 540 coupled to bus 530, and one or more I/O controllers 550, which in turn are coupled to peripheral devices such as cursor control device 560, keyboard 570, display(s) 580, etc. Each of I/O devices 560, 570, 580 may be capable of communicating with I/O controllers 550, for example, via a wired connection (e.g., serial port, Universal Serial Bus port) or wireless connection (e.g., Wi-Fi, Bluetooth, Near Field Communications Link, etc.). Other devices may include, for example, microphones, antennas/wireless transducers, phone detection modules, etc.

In various embodiments, computer system 500 may be a single-processor system including one processor 510A, or a multi-processor system including two or more processors 510A-N(e.g., two, four, eight, or another suitable number). Processors 510 may be any processor capable of executing program instructions. For example, in various embodiments, processors 510 may be general-purpose or embedded processors implementing any of a variety of instruction set architectures (ISAs), such as the x86, POWERPC®, ARM®, SPARC®, or MIPS® ISAs, or any other suitable ISA. In multi-processor systems, each of processors 510 may commonly, but not necessarily, implement the same ISA. Also, in some embodiments, at least one processor 510 may be a graphics processing unit (GPU) or another dedicated graphics-rendering device.

System memory 520 may be configured to store program instructions and/or data accessible by processor 510. In various embodiments, system memory 520 may be implemented using any suitable memory technology, such as static random-access memory (SRAM), synchronous dynamic RAM (SDRAM), nonvolatile/Flash-type memory, or any other type of memory. As illustrated, program instructions and data implementing certain operations and modules such as those described herein may be stored within system memory 520 as program instructions 525 and data storage 535, respectively. In other embodiments, program instructions and/or data may be received, sent, or stored upon different types of computer-accessible media or on similar media separate from system memory 520 or computer system 500.

A computer-accessible medium may include any tangible and/or non-transitory storage media or memory media such as electronic, magnetic, or optical media—e.g., disk or CD/DVD-ROM coupled to computer system 500 via bus 530. The terms "tangible" and "non-transitory," as used herein, are intended to describe a computer-readable storage medium (or "memory") excluding propagating electromagnetic signals, but are not intended to otherwise limit the type of physical computer-readable storage device that is encompassed by the phrase computer-readable medium or memory. For instance, the terms "non-transitory computer-readable medium" or "tangible memory" are intended to encompass types of storage devices that do not necessarily store information permanently, including for example, random access memory (RAM). Program instructions and data stored on a tangible computer-accessible storage medium in non-transitory form may further be transmitted by transmission media or signals such as electrical, electromagnetic, or digital signals, which may be conveyed via a communication medium such as a network and/or a wireless link.

In an embodiment, bus 530 may be configured to coordinate I/O traffic between processor 510, system memory 520, and any peripheral devices in the computer system, including network interface 540 or other peripheral interfaces, such as I/O devices 560, 570, 580. In some embodiments, bus 530 may perform any necessary protocol, timing, or other data transformations to convert data signals from one component (e.g., system memory 520) into a format suitable for use by another component (e.g., processor 510). In some embodiments, bus 530 may include support for devices attached through various types of peripheral buses, such as a variant of the Peripheral Component Interconnect (PCI) bus standard or the Universal Serial Bus (USB) standard, for example. In some embodiments, the function of bus 530 may be split into two or more separate components, such as a northbridge chipset and a southbridge chipset, for example. In addition, in some embodiments some or all the functionality of bus 530, such as an interface to system memory 520, may be incorporated directly into processor(s) 510A-N.

Network interface 540 may be configured to allow data to be exchanged between computer system 500 and other devices attached to a network, such as other computer systems, or between nodes of computer system 500. In various embodiments, network interface 540 may support communication via wired or wireless general data networks, such as any suitable type of Ethernet network, for example; via telecommunications/telephony networks such as analog voice networks or digital fiber communications networks; via storage area networks such as Fiber Channel SANs, or via any other suitable type of network and/or protocol.

I/O controllers 550 may, in some embodiments, enable communications with one or more display terminals, keyboards, keypads, touchpads, scanning devices, voice or optical recognition devices, mobile devices, or any other devices suitable for entering or retrieving data by one or more computer system 500. Multiple I/O controllers 550 may be present in computer system 500 or may be distributed on various nodes of computer system 500. In some embodiments, I/O devices may be separate from computer system 500 and may interact with one or more nodes of computer system 500 through a wired or wireless connection, such as over network interface 540.

As shown in FIG. 5, system memory 520 may include program instructions 525, configured to implement certain embodiments described herein, and data storage 535, comprising various data may be accessible by program instructions 525. In an embodiment, program instructions 525 may include software elements, which may be configured to affect the operations discussed in FIGS. 1 through 4. Program instructions 525 may be implemented in various embodiments using any desired programming language, scripting language, or combination of programming languages and/or scripting languages (e.g., C, C++, C#, JAVA®, JAVASCRIPT®, PERL®, etc.). Data storage 535 may include data that may be used in these embodiments (e.g., recorded communications, profiles for different modes of operations, etc.). In other embodiments, other or different software elements and data may be included.

A person of ordinary skill in the art will appreciate that computer system 500 is merely illustrative and is not intended to limit the scope of the disclosure described herein. The computer system and devices may include any combination of hardware or software that can perform the indicated operations. In addition, the operations performed by the illustrated components may, in some embodiments, be performed by fewer components or distributed across additional components. Similarly, in other embodiments, the operations of some of the illustrated components may not be provided and/or other additional operations may be available. Accordingly, systems and methods described herein may be implemented or executed with other computer system configurations.

The various operations described herein, particularly in connection with FIGS. 1 through 4, may be implemented in software executed by processing circuitry, hardware, or a combination thereof. The order in which each operation of a given method is performed may be changed, and various operations may be added, reordered, combined, omitted, modified, etc. It is intended that embodiment(s) described herein embrace all such modifications and changes and, accordingly, the above description should be regarded in an illustrative rather than a restrictive sense.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A controlled-environment facility resident smartwatch comprising:

a band configured to be affixed around a wrist of a controlled-environment facility resident, wherein the band is irremovable by the controlled-environment facility resident;

a watch body configured to store authentication information associated with the controlled-environment facility resident; and a transceiver configured to communicate with a controlled-environment facility management system to provide, as a result of a previous successful authentication of the smartwatch using the authentication information, at least one of a phone call, a video visitation session, an email message, a text message, or an Internet chat session for the controlled-environment facility resident using an account uniquely associated with the controlled-environment facility resident.

2. The controlled-environment facility resident smartwatch of claim 1, wherein the account comprises a resident commissary account used to purchase items from a commissary.

3. The controlled-environment facility resident smartwatch of claim 1, wherein the account comprises a resident communications account.

4. The controlled-environment facility resident smartwatch of claim 3, further comprising at least one of a Pre-Approved Contact (PAC) list or a Pre-Approved Number (PAN) list associated with the account, wherein the account is configured to ensure that the activities provided by the communications account are performed only with non-residents whose information are included in the PAC or the PAN.

5. The controlled-environment facility resident smartwatch of claim 1, wherein the transceiver is configured to:

receive media content from the controlled-environment facility management system; and play the media content for consumption by the controlled-environment facility resident.

6. The controlled-environment facility resident smartwatch of claim 5, wherein the media content comprises an alert message to provide an instruction or a warning.

7. The controlled-environment facility resident smartwatch of claim 1, further comprising:

a locking mechanism configured to releasably secure the band to the controlled-environment facility resident; and an unlocking mechanism configured to unlock the band from the controlled-environment facility resident without destroying the band.

8. The controlled-environment facility resident smartwatch of claim 7, further comprising an electrically conductive wire extending through the band, wherein the watch body is configured to detect breakage of the wire due to destruction of the band, and send an alert to controlled-environment facility personnel in response to the detected breakage.

9. A controlled-environment facility resident behavioral monitoring system comprising:

a plurality of controlled-environment facility resident smartwatches, each comprising:

a band configured to be affixed around a wrist of a controlled-environment facility resident, wherein the band is irremovable by the controlled-environment facility resident;

a watch body configured to store authentication information associated with the controlled-environment facility resident; and a transceiver configured to communicate with a controlled-environment facility management system, wherein the controlled-environment facility management system is configured to provide, as a result of a previous successful authentication of the smartwatch using the authentication information, at least one of a phone call, a video visitation session, an email message, a text message, an Internet chat session for the controlled-environment facility resident using an account uniquely associated with the controlled-environment facility resident.

10. The controlled-environment facility resident behavioral monitoring system of claim 9, wherein the account comprises a resident commissary account used to purchase items from a commissary.

11. The controlled-environment facility resident behavioral monitoring system of claim 9, wherein the account comprises a resident communications account.

12. The controlled-environment facility resident behavioral monitoring system of claim 11, further comprising at least one of a Pre-Approved Contact (PAC) list or a Pre-Approved Number (PAN) list associated with the account, wherein the account is configured to ensure that the activities provided by the communications account are performed only with non-residents whose information are included in the PAC or the PAN.

13. The controlled-environment facility resident behavioral monitoring system of claim 9, wherein the transceiver is configured to:

receive media content from the controlled-environment facility management system; and play the media content for consumption by the controlled-environment facility resident.

14. The controlled-environment facility resident behavioral monitoring system of claim 13, wherein the media content comprises an alert message comprising an instruction or a warning.

15. The controlled-environment facility resident behavioral monitoring system of claim 9, further comprising:

a locking mechanism configured to releasably secure the band to the controlled-environment facility resident; and an unlocking mechanism configured to unlock the band from the controlled-environment facility resident without destroying the band.

16. The controlled-environment facility resident behavioral monitoring system of claim 15, further comprising an electrically conductive wire extending through the band, wherein the watch body is configured to detect breakage of the wire due to destruction of the band, and send an alert to controlled-environment facility personnel in response to the detected breakage.

17. A controlled-environment facility resident behavioral monitoring method comprising:

configuring a controlled-environment facility resident smartwatch on a controlled-environment facility resident, wherein a band of the smartwatch is irremovable by the controlled-environment facility resident, wherein the smartwatch comprises a watch body configured to store authentication information associated with the controlled-environment facility resident, and a transceiver configured to communicate with a controlled-environment facility management system; and providing, by the controlled-environment facility management system as a result of a previous successful authentication of the smartwatch using the authentication information, at least one of a phone call, a video visitation session, an email message, a text message, a video visitation session, or an Internet chat session for the controlled-environment facility resident using an account uniquely associated with the controlled-environment facility resident.

18. The controlled-environment facility resident behavioral monitoring method of claim 17, wherein the account comprises at least one of a resident commissary account used to purchase items from a commissary or a resident communications account.

* * * * *